United States Patent
Isobe et al.

(10) Patent No.: US 6,552,083 B1
(45) Date of Patent: Apr. 22, 2003

(54) AGENTS INHIBITING CHRONIC REJECTION REACTIONS AFTER ORGAN TRANSPLANTATION

(75) Inventors: Mitsuaki Isobe, Shinjuku-ku (JP); Atsushi Izawa, Minamiazumi-gun (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/030,915
(22) PCT Filed: Jul. 7, 2000
(86) PCT No.: PCT/JP00/04529
    § 371 (c)(1),
    (2), (4) Date: May 23, 2002
(87) PCT Pub. No.: WO01/05394
    PCT Pub. Date: Jan. 25, 2001

(30) Foreign Application Priority Data

Jul. 16, 1999  (JP) .............................. 11/203270

(51) Int. Cl.[7] ..................... A61K 31/24; A61K 31/195
(52) U.S. Cl. .................. 514/563; 514/535; 514/567; 514/824; 514/885
(58) Field of Search ................... 514/535, 563, 514/567, 824, 885

(56) References Cited

U.S. PATENT DOCUMENTS 5,385,935 A  *  1/1995  Tamai et al. ................ 514/535

FOREIGN PATENT DOCUMENTS

EP          588518 A1      3/1994

* cited by examiner

*Primary Examiner*—Frederick Krass
(74) *Attorney, Agent, or Firm*—Sughrue Mion, PLLC

(57) ABSTRACT

The present invention relates to an agent for inhibiting diseases associated with chronic rejection after organ transplantation, such as transplanted heart-accelerated coronary arteriosclerosis, containing as an active ingredient N-(3,4-dimethoxycinnamoyl)anthranilic acid represented by formula:

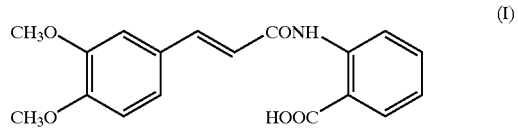

or a pharmaceutically acceptable salt thereof, which has an inhibitory effect on vascular thickening in transplanted hearts.

3 Claims, No Drawings

AGENTS INHIBITING CHRONIC REJECTION REACTIONS AFTER ORGAN TRANSPLANTATION

This application is a 371 of PCT/JP00/04529, filed Jul. 7, 2000.

TECHNICAL FIELD

This invention relates to a pharmaceutical composition useful as an agent for inhibiting chronic rejection after organ transplantation.

More particularly, it relates to an agent for inhibiting chronic rejection after organ transplantation which is characterized by containing N-(3,4-dimethoxycinnamoyl) anthranililc acid (generic name: tranilast) represented by formula:

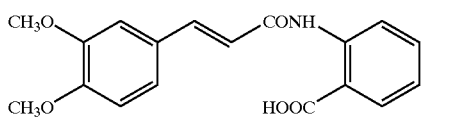

or a pharmaceutically acceptable salt thereof as an active ingredient.

BACKGROUND ART

While medical treatments by organ transplantations such as heart transplantation have been spreading worldwide, the primary subject of concern in organ transplantation is rejection response. Rejection responses after transplantation are roughly divided into acute rejection and chronic rejection. Immunosuppressants have been widely applied to acute rejection and played an important role in avoiding acute rejection. However, there is no treatments nor preventions to be taken against chronic rejection which are changes appearing in a transplanted organ after several months to several years from acceptance. The most dominant manifestation of chronic rejection is circumferential intimal thickening that occurs in every site irrespective of blood vessel sizes. For example, after heart transplantation, diffuse coronary arteriosclerosis such as transplanted heart-accelerated coronary arteriosclerosis is likely to occur due to circumferential intimal thickening. Progress of such arteriosclerosis results in organ blood flow reduction. In case of dysfunction, retransplantation is required. As described above, intimal thickening is a big problem governing the post-transplantation long-term prognosis, and early development of a drug having an inhibitory effect on chronic rejection response has been keenly demanded.

Tranilast represented by the above formula (I) is a drug widely employed in the treatment of allergic disorders such as bronchial asthma, allergic rhinitis, atopic dermatitis, and allergic conjunctivitis, and cutaneous disorders such as keloidal and hypertrophic scars. It is known to have, for example, an action of suppressing release of chemical mediators due to the allergic reaction and an action of suppressing excessive collagen accumulation by fibroblasts in cutaneous tissues.

It has also been reported that tranilast suppresses post-PTCA excessive proliferation of vascular smooth muscle cells in coronary arteries and is useful as an agent for treating and preventing coronary restenosis and arteriosclerosis after PTCA surgery and that it reduces atheroma deposition and is useful as an agent for inhibiting atherosclerosis (see Japanese Patent Applications Laid-Open Nos. Hei-6-135829 and Hei-9-227371). The former diseases develop for repairing the alto damaged in PTCA treatment, whereas chronic rejection as referred to in the present invention develops in blood vessels circumferentially in transplanted organs. They are embryologically utterly different diseases. Further, the latter disease is atherosclerosis, whereas chronic rejection as referred to in the invention is pathologically quite different therefrom, involving no atheroma development. It is not known at all that tranilast inhibits chronic rejection after organ transplantation.

DISCLOSURE OF THE INVENTION

The present inventors have conducted extensive researches seeking for a compound having an inhibitory effect on chronic rejection after organ transplantation. As a result, they have found that tranilast represented by the above formula (I) has an action of markedly inhibiting vascular intimal thickening in the transplanted organ after organ transplantation and an action of inhibiting infiltration of lymphocytes into tissue which accompanies organ transplantation, and is therefore extremely useful as an agent for inhibiting chronic rejection after organ transplantation. The present invention was accomplished based on these findings.

That is, the present inventors have confirmed that tranilast significantly inhibits intimal thickening which circumferentially occurs in coronary arteries of transplanted hearts by the in vivo experimentation using a mouse heart transplantation model.

Furthermore, they have also confirmed that tranilast inhibits infiltration of lymphocytes into tissue which is one of immune responses after heart transplantation by the in vivo experimentation using a mouse heart transplantation model.

Consequently, tranilast exhibits excellent inhibitory effects on infiltration of lymphocytes into tissue and transplanted heart vascular thickening which to chronic rejection induced after heart transplantation and is a useful compound as an agent for inhibiting chronic rejection after organ transplantation. Therefore, it is effective in inhibiting chronic rejection after organ transplantation, such as various types of arteriosclerosis occurring after transplantation of organs, e.g., hearts, livers, kidneys and lungs, for example, transplanted heart-accelerated coronary arteriosclerosis.

Accordingly, tranilast or a pharmaceutically acceptable salt thereof serves as an active ingredient to provide a pharmaceutical composition useful as an agent for inhibiting chronic rejection after organ transplantation.

Various processes for preparing tranilast and its salts as an active ingredient are known. They are easily prepared by processes described in the literature (e.g., Examined Japanese Patents Publication Nos. Sho-56-40710, Sho-57-36905, Sho-58-17186, Sho-58-48545, Sho-58-55138, Sho-58-55139, Hei-1-28013, Hei-1-50219 and Hei-3-37539).

Pharmaceutically acceptable salts of tranilast include salts with inorganic bases, such as a sodium salt and a potassium salt, and salts with organic amines, such as morpholine, piperidine and pyrrolidine, or amino acids.

In applying the pharmaceutical composition of the invention in actual treatment various dosage forms are available for choice according to use. Such dosage forms include powders, granules, fine granules, dry syrups, tablets, capsules, and injections.

These pharmaceutical compositions may be prepared in conventional manner by commonly employed procedures suitable for dosage forms, that is, by mixing with, or diluting with or dissolving in, appropriate pharmaceutical additives, such as excipients, disintegrants, binders, lubricants, diluents, buffers, isotonic agents, antiseptics, moistening agents, emulsifiers, dispersing agents, stabilizing agents, dissolution assistants, and so forth.

For example, powders are prepared by thoroughly admixing tranilast or a pharmaceutically acceptable salt thereof with appropriate excipients, lubricants and the like as occasion demands.

Tablets are prepared by adding appropriate excipients, disintegrants, binders, lubricants and the like to tranilast or its pharmaceutically acceptable salt as occasion demands and punching the mixture into tablets in conventional manner. If desired, the tablets may be coated to obtain film-coated tablets, sugar-coated tablets, enteric-coated tablets, etc.

Capsules are prepared by thoroughly admixing tranilast or its pharmaceutically acceptable salt with appropriate excipients, lubricants and the like as occasion demands and encapsulating the mixture in appropriate capsules. The mixture may be processed Into granules or particles before encapsulation.

In using the pharmaceutical composition of the invention in actual treatment, the active ingredient, i.e., tranilast or a pharmaceutically acceptable salt thereof, can be administered at a dose ranging from about 100 to 1000 mg for oral administration per day for adult human and ranging from about 20 $\mu$g to 300 mg for parenteral administration per day for adult human, which is appropriately decided depending on the body weight, age, sex, etc. of each patient.

The present invention is further illustrated in more detail by way of the following Examples.

EXAMPLE 1

Test for Confirming Inhibitory Activity Against Intimal Thickening in Transplant Organ After Organ Transplantation In a transplantation test, 4 to 6-week-old DBA/2 male mice each weighing 20 to 25 g (available from Charles River Laboratories) were used an donor animals, and 4 to 6-week-old B10D2 male mice each weighing 20 to 25 g (ava from Charles River Laboratories) were used as recipient animals. From three days before testing, mice in a control group were fed on a standard diet, and mice in a drug-treated group were given a 0.25% or 0.5% tranilast-containing diet (CE-2). On the day of testing, the heart was excised from a donor mouse and transplanted into the abdomen of a recipient mouse in accordance with the procedures described in the literature (Science, vol. 255, pp. 1125–1127 (1992)). Fourteen and twenty-eight days from the transplantation, the transplanted heart was excised and placed in formalin. Three specimens (thickness: 5 m) were sliced from different sites of the excised heart. Each slice was stained with Elastica van Geison stain, and the coronary arteries were observed under a microscope to calculate a vascular stenosis ratio according to the following equation:

Vascular stenosis ratio (%)=[(area inside of elastica −lumen area)/ area inside of elastica]×100

The test results were as shown in Table 1 below, proving that tranilast dose-dependently significantly inhibits vascular thickening in a transplanted heart.

TABLE 1

|  | Vascular Stenosis Ratio (%) | |
|---|---|---|
|  | 14-days post-operation | 28-days post-operation |
| Control group | 70.3 | 73.3 |
| 0.25% Tranilast-containing feed group | 55.5 | 61.9 |
| 0.5% Tranilast-containing feed group | 45.5 | 47.7 |

EXAMPLE 2

Test for Evaluating Rejection in Transplant Organ After Organ Transplantation

The degree of rejection in the hearts transplanted to and excited from the recipient mice in the same manner as in Example 1 was evaluated in terms of the degree of infiltration of lymphocytes into the tissue in accordance with the Working Formation of the International Society for Heart and Lung Transplantation and with the following criteria.

0 . . . No infiltration of lymphocytes into the tissue was seen.

1 . . . Slight infiltration of lymphocytes into the tissue was observed.

2 . . . Medium infiltration of lymphocytes into the tissue was observed.

3 . . . Severe infiltration of lymphocytes into the tissue was observed.

The results of evaluation were as shown in Table 2 below, showing that tranilast alleviates infiltration of lymphocytes into the tissue.

TABLE 2

|  | Degree of rejection | |
|---|---|---|
|  | 14-days post-operation | 28-days post-operation |
| Control group | 2.07 | 2.88 |
| 0.25% Tranilast-containing feed group | 1.70 | 2.38 |
| 0.5% Tranilast-containing feed group | 1.80 | 2.08 |

Industrial Applicability

Tranilast represented by the above formula (I) and a pharmaceutically acceptable salt thereof have excellent inhibitory effects on chronic rejection after organ transplantation. The present invention provides an agent for inhibiting chronic rejection after organ transplantation, which exhibits an excellent inhibitory effect on chronic rejection after organ transplantation.

What is claimed is:

1. A method for inhibiting chronic rejection after organ transplantation which comprises administering to a subject in need thereof a therapeutically effective amount of N-(3, 4-dimethoxycinnamoyl)anthranilic acid represented by formula:

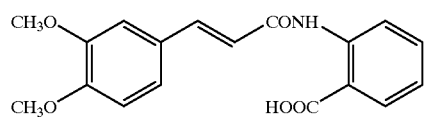

or a pharmaceutically acceptable salt thereof.

2. A method for inhibiting chronic rejection after organ transplantation according to claim 1 wherein the chronic rejection is post-transplantation arteriosclerosis.

3. A method for inhibiting chronic rejection after organ transplantation according to claim 2 wherein the chronic rejection is transplanted heart-accelerated coronary arteriosclerosis.

* * * * *